United States Patent [19]

Weissman

[11] 4,431,417

[45] Feb. 14, 1984

[54] VARIABLE CONNECTOR FOR FIXED AND REMOVABLE DENTAL PROSTHESES

[76] Inventor: Bernard Weissman, 225 East 48th St., New York, N.Y. 10017

[21] Appl. No.: 427,767

[22] Filed: Sep. 29, 1982

Related U.S. Application Data

[63] Continuation-in-part of Ser. No. 188,356, Sep. 18, 1980, Pat. No. 4,355,979, which is a continuation-in-part of Ser. No. 70,247, Aug. 27, 1979, Pat. No. 4,260,383.

[51] Int. Cl.$^3$ ............................................... A61C 13/22
[52] U.S. Cl. ................................................... 433/182
[58] Field of Search ......................... 433/181, 182, 183

[56] References Cited

U.S. PATENT DOCUMENTS

| | | | |
|---|---|---|---|
| 339,958 | 4/1886 | White | 433/183 |
| 1,211,494 | 1/1917 | Shaw | 433/181 |

Primary Examiner—Robert Peshock
Attorney, Agent, or Firm—Goodman & Teitelbaum

[57] ABSTRACT

A variable connector for supporting a dental prosthesis between opposing spaced apart supporting teeth, the connector including a pair of elongated bar-like body members, each of the body members being disposable in its own channel in at least one supporting tooth on opposite sides of the prosthesis being retained. At least one tubular member depends from each body member and is received in a respective bore provided in the respective supporting tooth, each bore extending through a bottom wall of its respective channel. Each tubular member includes an axial opening extending therethrough. A pair of elongated straps are provided with each strap having at least one depending pin, the straps being respectively disposable over a body member with the pins extending into the axial openings of the tubular member of that body member. The straps terminate in arms which are disposed outwardly from the supporting teeth. A securing device is located on the arms, being disposed within the space between the supporting teeth for providing securement of said arms. The prosthesis is properly supported by the arms and the securing device.

14 Claims, 17 Drawing Figures

VARIABLE CONNECTOR FOR FIXED AND REMOVABLE DENTAL PROSTHESES

RELATIONSHIP TO OTHER APPLICATIONS

This application is a continuation-in-part of co-pending application Ser. No. 188,356 filed Sept. 18, 1980, now U.S. Pat. No. 4,355,979 issued Oct. 26, 1982, for a "Lingual Dental Splint Device", which in turn is a continuation-in-part application of Ser. No. 070,247, filed Aug. 27, 1979 for a "Dental Retaining Splint" and now U.S. Pat. No. 4,260,383 issued Apr. 7, 1981.

This invention also relates, in part, to U.S. Pat. No. 4,348,181 issued Sept. 7, 1982 to the assignee of the present invention, and to U.S. Pat. No. 3,089,242 issued May 14, 1963 to the inventor of the present application. All of the aforementioned applications and patents are herein incorporated by reference.

BACKGROUND OF THE INVENTION

This invention relates to denistry in general, and more particularly to a connector which can support either a fixed or a removable dental prosthesis positioned between opposing, spaced apart, supporting teeth.

There are various dental prostheses which are inserted in the patient's mouth and retained in place between existing dentition. In many cases, the existing dentition is utilized as the support for the dental prosthesis. In some situations, the dental prosthesis is of a fixed type whereby, once inserted, it is permanently retained in place. At other times, the prosthesis is of a removable type whereby it can be removed for cleaning or maintenance, and the like. Even a removable prosthesis, however, must be sufficiently secured in place to prevent accidental displacement during continued use.

In the aforementioned U.S. Pat. No. 3,089,242, there is described a holding device for a removable dental prosthesis where one member having a ring is attached to the dental prosthesis and is slipped down into a channel of a second member secured onto the side of a fixed tooth. A modification of this device is described in the aforementioned U.S. Pat. No. 4,348,181 wherein two sections are provided, one section being secured to the side of a fixed tooth and the cooperating other section being secured within the dental prosthesis. The two sections are interconnected by a spring loaded plunger which can engage in a recess formed in the other section. The two sections can also interlock with each other.

With these aforementioned retaining devices, only a removable prosthesis can be held in place. Furthermore, it is often difficult to properly position the section of the holding device which is in the side of the fixed tooth so that it will be alligned with the mating section in the removable section. Also, at times, greater support may be needed than can be provided with these devices, especially where large dental prosthesis involving numerous teeth must be held in place.

In the aforementioned parent applications, there is described a dental splint which is utilized for retaining adjacent teeth in place by splinting one tooth to an adjacent tooth. In such device, there is provided a body member having tubular portions extending therefrom, the tubular portions including axial openings therethrough. The body member is positioned in a channel spanning between the adjacent teeth to be splinted together. The tubular members are positioned upwardly and the axial openings are utilized for drilling pilot holes through the base wall of the channel in the adjacent teeth. With the splint removed, the pilot holes are reamed to enlarge them, and then, the body member is replaced in the channel with the tubular members now extending downwardly into the reamed holes. After the channel is covered with dental restorative material, the body member forms a dental retaining splint spanning between the adjacent teeth and holding one tooth in place adjacent to its supporting tooth. U-shaped clips can be inserted into the tubular members to provide additional retention when the splint is inserted laterally in the teeth to splint them together.

While the body member described in the parent applications has been utilized for splints, it has not been utilized for the support of a fixed or removable prosthesis. Accordingly, the problem of suitably supporting a dental prosthesis, either fixed or removable, between opposing, spaced apart, supporting teeth requires a proper solution. Also, the type of support and holding device that is used, should be one that can support different lengths of prostheses. The connector should be of the type whose capabilities can be utilized for prostheses of different types and different lengths and, should still provide for the proper support.

SUMMARY OF THE INVENTION

Accordingly, it is an object of the present invention to provide a connector which can be utilized for supporting a dental prosthesis between opposing, spaced apart, supporting teeth.

Another object of the present invention is to provide a connector which can be utilized for supporting a removable prosthesis or a fixed prosthesis, spaced between supporting teeth.

Still another object of the present invention is to provide a connector which can be utilized with prostheses of varied lengths and types, supported between spaced apart, supporting teeth.

Still a further object of the present invention is to provide a connector which can be secured into one or more supporting teeth, and which has arms extending into the space between the supporting teeth, for thereby retaining either a fixed or removable dental prosthesis in place.

Yet a further object of the present invention is to provide a connector which can be utilized for supporting a dental prosthesis spanning between spaced apart supporting teeth, and which can also be utilized when adjacent supporting teeth are splinted together.

In accordance with the present invention, there is provided a connector for supporting a dental prosthesis between opposing, spaced apart, supporting teeth. The connector includes a pair of elongated bar-like body members. Each of the body members is disposable in its own channel in at least one supporting tooth on opposite sides of the prosthesis being retained. At least one tubular member depends from each of the body members for being received in a respective bore provided in the respective supporting tooth. The bores extend through a bottom wall of the respective channel. Each of the tubular members includes an axial opening extending therethrough. A pair of elongated straps are provided with each strap having at least one depending pin. Each of the straps is disposable over a respective one of the body members with the pin from that strap extending into the axial opening in the tubular member on that body member. The straps terminate in arms which extend from the supporting teeth. A securing device is provided on portions of the arms, with the securing device being located in the space between the supporting teeth.

In one embodiment of the present invention, the arms are cantilevered from the straps into the space between the supporting teeth. The distal ends of the arms of the two opposing straps overlap to thereby define a continuous bridge across the space between the supporting teeth. A sleeve serves to secure the overlapping ends together.

In another embodiment of the present invention, the arms terminate in downwardly bent sections which lie against the side of the supporting teeth. Secured onto each of these downwardly bent sections is one part of a securement device for removably securing the dental prosthesis between the supporting teeth. The other part of the securement device is retained by the dental prosthesis.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like reference characters designate like parts.

DETAILED DESCRIPTION OF THE PREFERRED EMBODIMENTS

Figure 1:
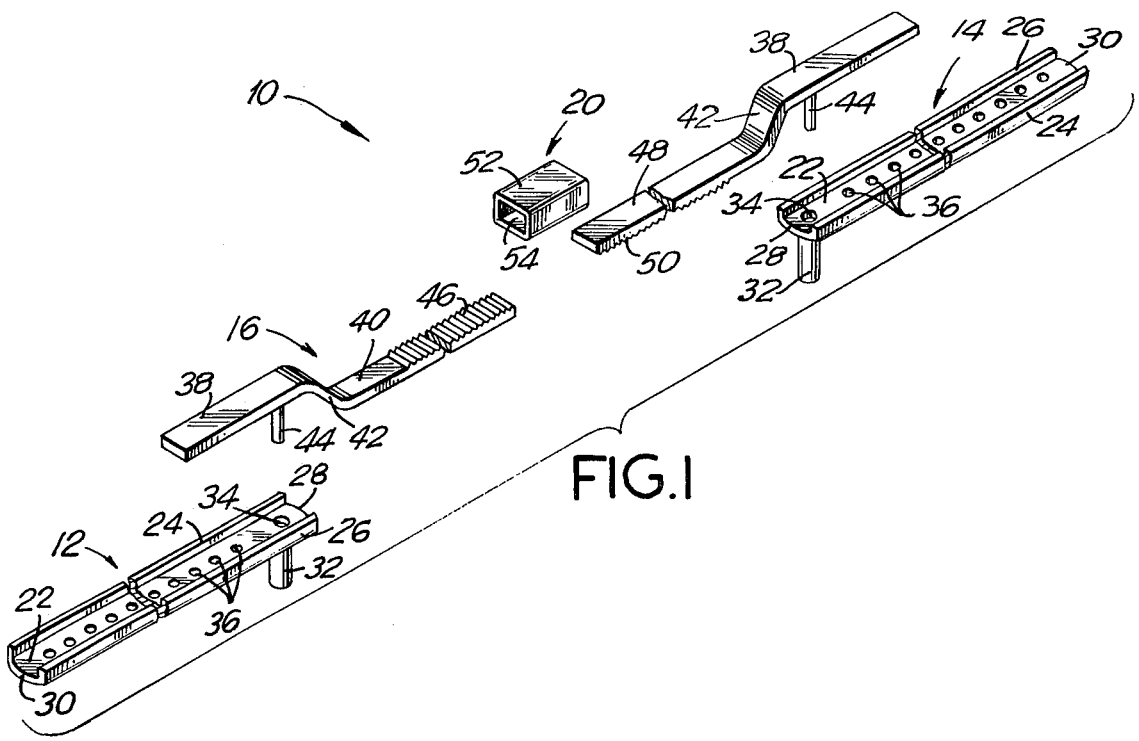
FIG. 1 is a perspective exploded view illustrating the variable connector of the present invention for use with a fixed dental prosthesis.

Referring now to FIG. 1, the variable connector of the present invention is shown generally at 10 and comprises a pair of bar-like body members 12 and 14, a pair of straps 16 and 18, and a sleeve retainer 20. The bar-like body member 12 is formed of an elongated section including a base wall 22 with upstanding side walls 24, 26 so as to define a u-shaped channel or trough. For convenience, both distal ends 28, 30 of bar-like member 12 are rounded in order to eliminate sharp corners. Depending from the bar-like body member 12, adjacent end 28, is a tubular member 32 having an axial opening 34 extending therethrough. Additionally, there is provided an array of openings 36 linearly spanning the length of the base wall 22 of the bar-like body member 12.

The particular length of the bar-like body member 12 can be adjusted by the dentist in situ. It can be preformed in fixed lengths, and can be suitably trimmed or cut by the dentist in situ so as to permit the body member to fit properly in the particular dental structure being repaired.

The strap 16 is formed of a continuous strip of material having a substantially rectangular cross sectional configuration. The strap 16 includes a horizontal section 38 which supports a cantelevered arm 40. The arm 40 is offset by means of the downwardly angled intermediate section 42, whereby the arm 40 lies in a plane lower than the plane of the horizontal section 38. A downwardly depending pin 44 extends beneath the horizontal section 38. At the distal end of the arm 40 there is provided the grooved or serrated surface 46 on the upper side of the arm 40.

The structure of the bar-like body member 14 is exactly identical to the structure of the bar-like body member 12, and is accordingly not described in detail, whereby like reference characters have been provided thereto. Similarly, the strap 18 is substantially identical with the strap 16, and is also not described in detail, whereby like reference characters have been provided to like parts. However, it should be appreciated that the arm 48 extending from the strap 18 includes its serrated surface 50 on the lower side thereof. Thus, the serrated surfaces 46 and 50 will be facing each other. It should be understood that for convenience, both the upper and lower surfaces of both arms 40 and 48 of the straps 16 and 18 could be serrated so that the straps 16 and 18 would be intechangeable. The bar-like body members 12, 14 being idential as noted above, are therefore interchanged.

The sleeve 20 includes a substantially rectangular member 52 having an internal passageway 54 therethrough corresponding to approximately twice the thickness of each of the straps 16, 18. In this way, both the arms 40 and 48 can be inserted within the opening 54 of the sleeve 20 from opposite ends thereof, with the abutting serrated surfaces 46 and 50 overlying and locking into each other. The sleeve 20 can then be crimped or clamped onto the arms 40, 48 to lock them in place.

Figure 2:
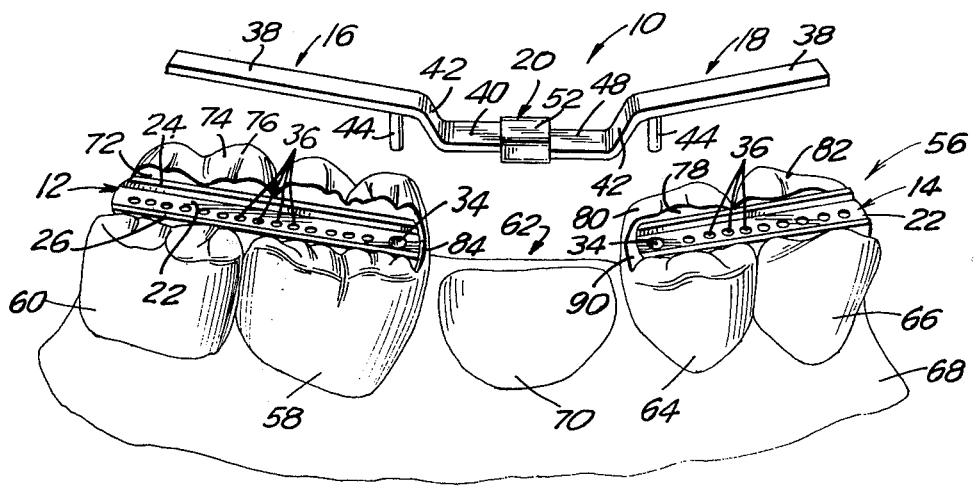
FIG. 2 is a perspective view illustrating the use of the connector of FIG. 1 in spanning the space between the supporting teeth in which a prosthesis is to be permanently inserted.
Figure 3:
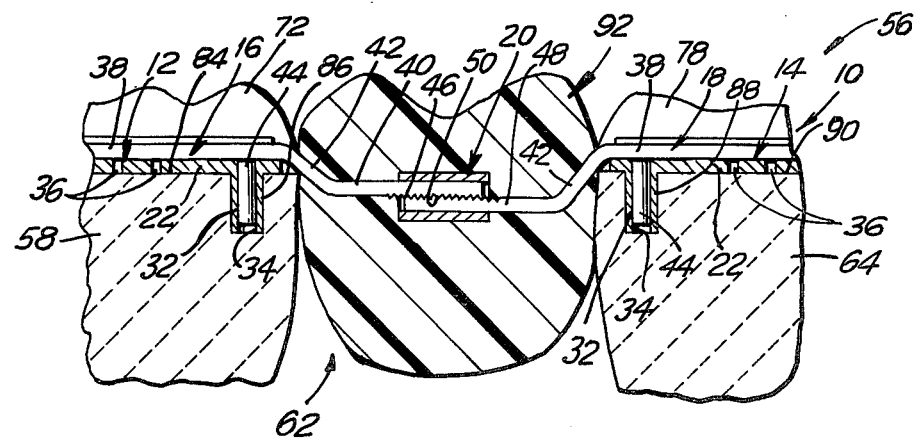
FIG. 3 is a fragmented cross sectional elevational view showing the connector of FIG. 1 secured in place in the supporting teeth with a dental prosthesis permanently positioned between the supporting teeth.

Referring now to FIGS. 2 and 3, the utilization of the connector 10 of FIG. 1 for holding a fixed dental prosthesis, will now be described. It is presumed that in the patient's mouth section 56, there are provided supporting teeth 58, 60 on one side of a space 62, and another pair of supporting teeth 64, 66 on the opposing side of the space 62. All the teeth extend upwardly from a gum section 68, whereby the space 62 includes a depression 70 from which a tooth may have previously been extracted. A permanent dental prosthesis must now be inserted in the dental area or space 62, with the dental prosthesis being supported between the opposing supporting teeth 58, 64. The supporting teeth on either side of the space 62 will therefore be utilized for supporting and retaining the permanent dental prosthesis.

Initially, a channel 72 is formed into the occlusal surface 74 of the tooth 60 and into the occlusal surface 76 of the tooth 58. A similar channel 78 is formed into the occlusal surface 80 of the supporting tooth 64 and the occlusal surface 82 of the supporting tooth 66. A bore 86 is then formed through the base wall 84 of the channel 72 in tooth 58, and a corresponding bore 88 is formed in the base wall 90 of the channel 78 in the tooth 64.

In forming the bores 86, 88, the method described in connection with the aforementioned parent applications can be utilized. Specifically, after the channels 72, 78 are formed, a layer of temporary adhesive, such as wax or other suitable material can be disposed on the base walls 84, 90 of the channels. The respective bar-like body members 12, 14, can be positioned in the respective channels 72, 78 with the tubular members 32 thereof extending upwardly from the channels. The bar-like body members 12, 14 are temporarily held in the channels by the temporary adhesive.

A pilot drill can then be inserted into the axial opening of the tubular members 32, and initial pilot holes are formed in the respective teeth 58, 64. Typically, the drill bit has a predetermined length in order to obtain the desired length of the pilot holes. After the pilot holes have been made, the bar-like body members 12, 14 are respectively removed from their channels 72, 78. Another dental drill is now used to ream the bores in the teeth where the pilot holes function as lead holes for the drill bits in the formation of the bores 86, 88. Here again, the drill bits can have a predetermined length in order that the bores 86, 88 have a desired selected depth.

The bar-like body members 12, 14 can now be reinserted into the channels, this time with the tubular members 32 extending downwardly and wherein the tubular members 32 are now positioned in the previously formed bores 86, 88. Suitable permanent adhesive can now be utilized to permanently retain the bar-like body members 12, 14 in place.

When inserting the bar-like body members 12, 14, they can be suitably cut to size after the channels have been formed, so that the length of the bar-like body members 12, 14 will be suitably accommodated within the channels 72, 78. The apertures 36 formed in the bar-like body members 12, 14 are available for receiving therethrough additional screws or other fasteners which are inserted into the supporting teeth to further secure the bar-like body members in place within the channels. Thus, they can be used for proper location of other holes which can be drilled through the base walls 88, 90 of the channels 72, 78, whereby tapping screws or the like can be inserted through the apertures 36 into the supporting teeth.

Furthermore, these holes or apertures 36 provide escape means for the permanent adhesive material during the permanent retainment of the bar-like body members 12, 14, whereby the permanent adhesive can flow upwardly and through the apertures 36 to escape from the bottom of the channels for the proper positioning of the bar-like body members 12, 14 within the channels 72, 78. The permanent adhesive in the apertures 36 will also function to secure or anchor the bar-like body members 12, 14 within the channels 72, 78.

With the bar-like body members 12, 14 permanently secured within the channels 72, 78, the respective straps 16, 18, can now be positioned in the corresponding body members 12, 14. The straps are inserted between the opposing side walls 24, 26 of the bar-like body members so that the straps sit on the base walls 22 of the body members 12, 14. It will be appreciated, that the straps 16, 18 nestingly fit within the U-shaped trough of the respective bar-like body members so that the straps are snugly received therein. Thus nesting arrangement prevents angular and transverse displacement of the straps with respect to the bar-like body members. Additionally, the thickness of straps 16, 18 are substantially equal to the wall height of the bar-like body members so that the straps substantially fill the trough-like shape of the body members 12, 14.

The pins 44 of the straps are inserted into the axial openings 34 of the tubular members 32, and thereby anchor the straps 16, 18 so as to prevent longitudinal movement with respect to the respective bar-like body members 12, 14. With the straps suitably secured within their respective bar-like body members, the arms 40, 48 will extend in a cantilever fashion across the space 62 and are positioned so that the ends overlap with the serrated edges 46, 50 interlocking onto each other. The sleeve 20, which is first prepositioned on one of the arms, is then slid over the abutting edges to that it holds the abutting edges of the arms 40, 48 in place. The sleeve 20 can then be crimped, clamped, etc., thereby securing it in place.

With the arrangement described, the arms form a bridge across the space 62. A suitable dental prosthesis 92 can then be positioned in the space 62, being disposed about the arms 40, 48 so that the prosthesis is secured to the arms. The prosthesis 92 can be formed in accordance with well known standard procedures, either by the dentist or by the laboratory technician. Once attached, however, it is supported by the arms between the adjacent teeth and will permanently remain in place. The channels can be filled with dental restorative material after the prosthesis is positioned between the supporting teeth.

It is noted, that the straps 16, 18 can be suitably cut in situ once their position is determined. Their remote ends can be cut so as to properly terminate at proximatly the ends of the bar-like body members 12, 14 supporting them. Similarly, the overlapping ends can also be suitably cut so that they properly fit within the sleeve 20.

Although the embodiment shown in FIG. 2 utilizes two supporting teeth on either side of the space 62, it should be appreciated that only one tooth on each side need be utilized or, even more than two teeth on each side can be utilized. When providing more than one supporting tooth on each side of the space 62, the additional teeth provide further retention for the bar-like body members and the straps, and therefore, additional support for the dental prosthesis 92. Furthermore, although only a single tubular member 32 was shown for each bar-like body member, it should be understood that additional tubular members could be utilized either in the same teeth, or in adjacent teeth.

Figure 4:
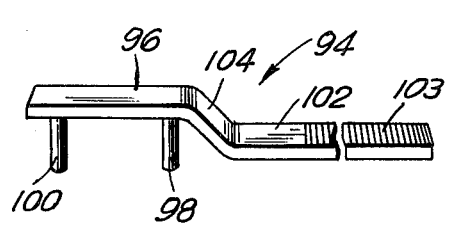
FIG. 4 is a perspective view showing a modification of the strap of FIG. 1 having two depending pins for providing additional retention.
Figure 5:
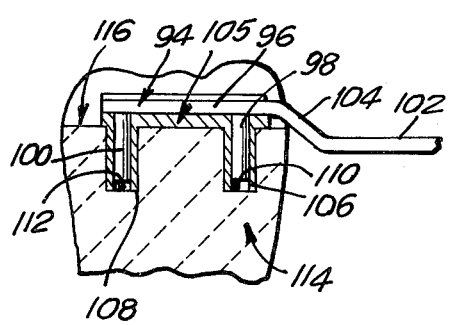
FIG. 5 is a fragmented cross sectional elevational view showing the positioning of the modified strap of FIG. 4 in place on a supporting tooth.

More specifically, referring now to FIGS. 4 and 5, there is shown a modified strap 94 having a horizontal section 96 from which depends a pair of spaced apart pins 98, 100. The cantilevered arm 102 is serrated at 103 and again offset by the section 104. The strap 94 would be used in cooperation with an overlapping section from another similar strap, being joined together by the sleeve 20, as heretofore described, so that a full showing and description of the other strap is not thought necessary.

When the strap of FIG. 4 is inserted in a tooth, as shown in FIG. 5, it would be received within a splint, such as a bar-like body member 105 having a trough-like shape and two tubular members 106, 108 having axial openings therethrough, which are in turn received in a pair of bores 110, 112 formed in a single tooth 114. The bar-like body member 105 would be positioned within the channel 116 and initially utilized to form the two bores 110, 112, using the method heretofore described. The pins 98, 100 of the strap 94 are positioned in the tubular members of the bar-like body member 104. The use of two bores in a single tooth, provides additional retaining of the strap, and also provides for better support of the dental prosthesis.

Figure 6:
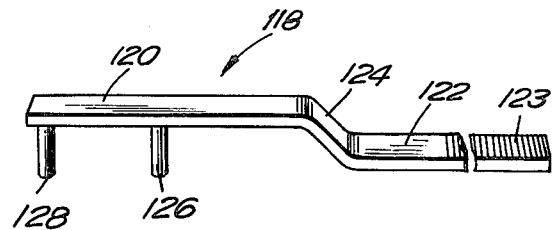
FIG. 6 is a perspective view of another modified strap of the type shown in FIG. 1 for use in splinting together adjacent supporting teeth, in addition to being used for retaining a permanent prosthesis.
Figure 7:
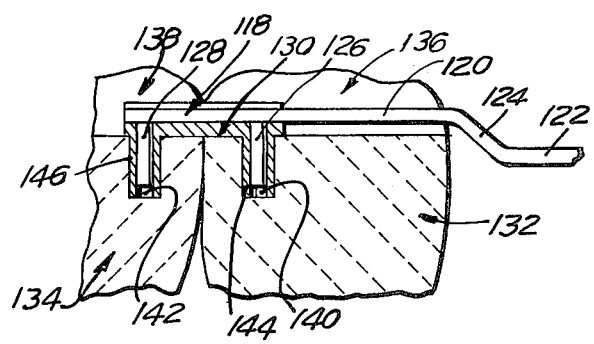
FIG. 7 is a fragmented cross sectional elevation view showing the positioning of the modified strap of FIG. 6 in adjacent supporting teeth.

Referring now to FIGS. 6 and 7, there is shown another modified strap also utilized simultaneously with a splint, so as to provide retention between adjacent supporting teeth. More particularly, there is shown a strap 118 having an elongated horizontal section 120. An arm 122 is serrated at 123 and supported in cantilevered fashion by means of the offset intermediate section 124. A pair of depending pins 126, 128 extend from the lower surface of the horizontal section 120. It should be appreciated, that the pins 126, 128 are spaced a substantial distance from the offset arm 122, but are spaced apart the same distance as the pins 98, 100 of the above mentioned strap 94.

As shown in FIG. 7, a splint such as a bar-like body member 130 having a trough-like shape is utilized for retaining together the adjacent teeth 132, 134. A channel 136 is initially formed in the tooth 132 with a cooperating corresponding channel 138 formed in the adjacent tooth 134. A pair of bores 140, 142 are respectively formed into the base walls of the channels 136, 138. The tubular members 144, 146 are inserted into the bores 140, 142, and the strap 118 is inserted so that the respective pins 126, 128 are received within the axial openings of the tubular members 144, 146. Utilizing the embodiment of FIGS. 6 and 7, the bar-like body member 130 serves as a splint for splinting together adjacent teeth, and also serves to better support the permanent dental prosthesis connected to the cantelevered arm 122. Here again, it is not thought necessary to show or describe the cooperating other strap which is joined to the strap 118 by the sleeve 20, in the manner heretofore described.

It will be noted that when inserting the pins of the straps into the tubular members of the splint, the length of the pins are adjusted so that they do not extend to the bottom of the bores formed in the channels. This permits some of the adhesive material to enter into the bottom of the tubular members, and prevents cracking, and provides for other useful results, as was heretofore described in the parent applications.

Figure 8:
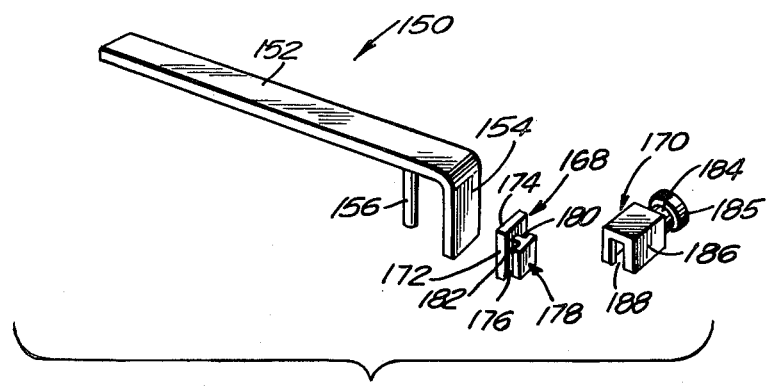
FIG. 8 is a perspective exploded view illustrating a strap in accordance with another embodiment of the present invention for use in conjunction with a removable dental prosthesis.

Referring now to FIG. 8 there is shown another embodiment of a strap 150, in accordance with the present invention. The strap 150 is formed of a single length of material including a horizontal section 152 and a downwardly depending distal arm 154. A pin 156 depends from the horizontal section 152.

Secured onto the front face of the depending arm 154 is a male member 168 of a securement device, the female member 170 thereof being available for insertion within a dental prosthesis, as will hereinafter be explained.

Figure 9:
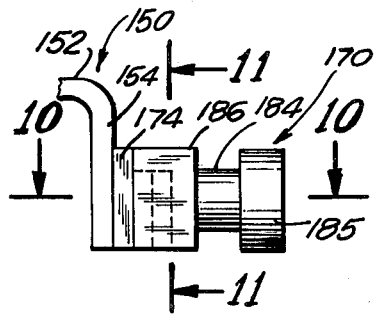
FIG. 9 is a fragmented side elevational view of the arm at the end of the strap of FIG. 8, showing the arm supporting the securement device for removably securing the dental prosthesis in position between supporting teeth.
Figure 11:
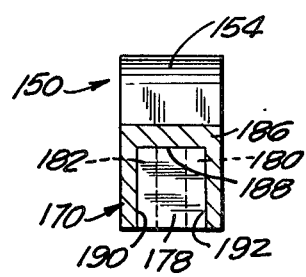
FIG. 11 is a cross sectional view taken along lines 11—11 of FIG. 9.
Figure 10:
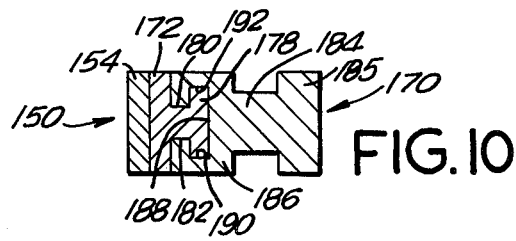
FIG. 10 is a cross sectional view taken along lines 10—10 of FIG. 9.

The particular securement device is of a type heretofore described in U.S. Pat. Nos. 3,089,242 and 4,348,181. More particularly, as shown in FIG. 8-10, the male member 168 includes a plate 172 having a rear surface 174 which would be secured onto the forward surface of the arm 154. Extending from the opposing surface 176 of the plate 174 is a projection 178 having a pair of opposing undercuts 180, 182 formed on either side thereof.

The female member 170 includes a tubular body portion 184 having an enlarged tubular foot portion 185 extending at one end thereof and a forward housing or head portion 186 at the opposite end thereof. The head portion 186 is of substantially rectangular configuration including a U-shaped channel 188 extending therein. A pair of undercuts 190, 192 are formed internally in the channel 188 of the head section 186 so as to securely receive the projection 178 from the male member 168.

The female member 170 can therefore slide downwardly over the projection 178 of the male member 168, and will be securely retained in place. The peripheral sides of the head section 186 on the female member 170 corresponds to the shape of the plate 174 so that when in place, a continuous peripheral housing is achieved. Because of the U-shape channel 188 of the housing 186, and the undercuts 180, 182 on either side of the projection 178, as well as the undercuts 190, 192 internal of the channel walls, any rotation between the female and male member is avoided. Although the male and female members 168, 170 will be securely held together, the securement device could also be formed with a spring loaded plunger disposed in the female member 170 which is received within a recess formed in the projecting member 178 of the male member 168, as described in the aforementioned patent. Other similar securement devices could also be utilized.

Figure 12:
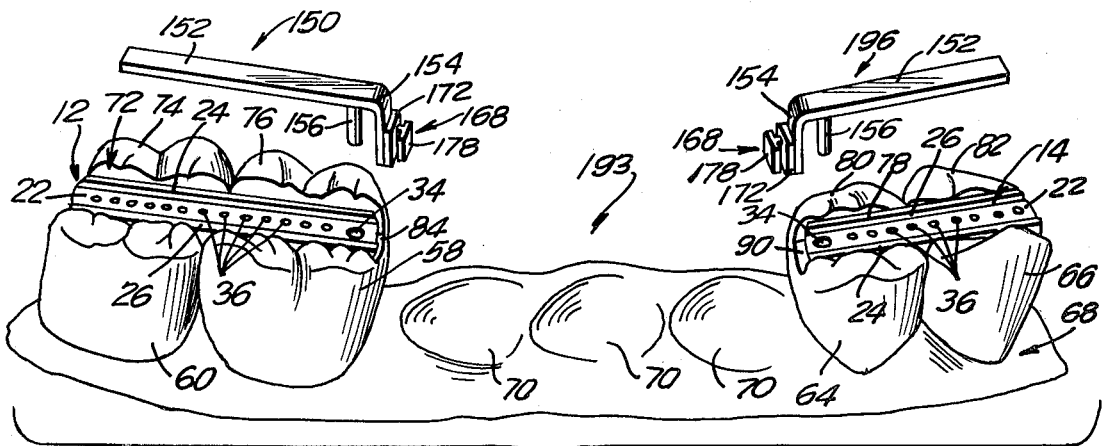
FIG. 12 is a perspective view showing the positioning of a pair of straps of the type shown in FIG. 8, which are positioned in spaced apart supporting teeth, wherein a removable dental prosthesis is to be inserted in the space.
Figure 13:
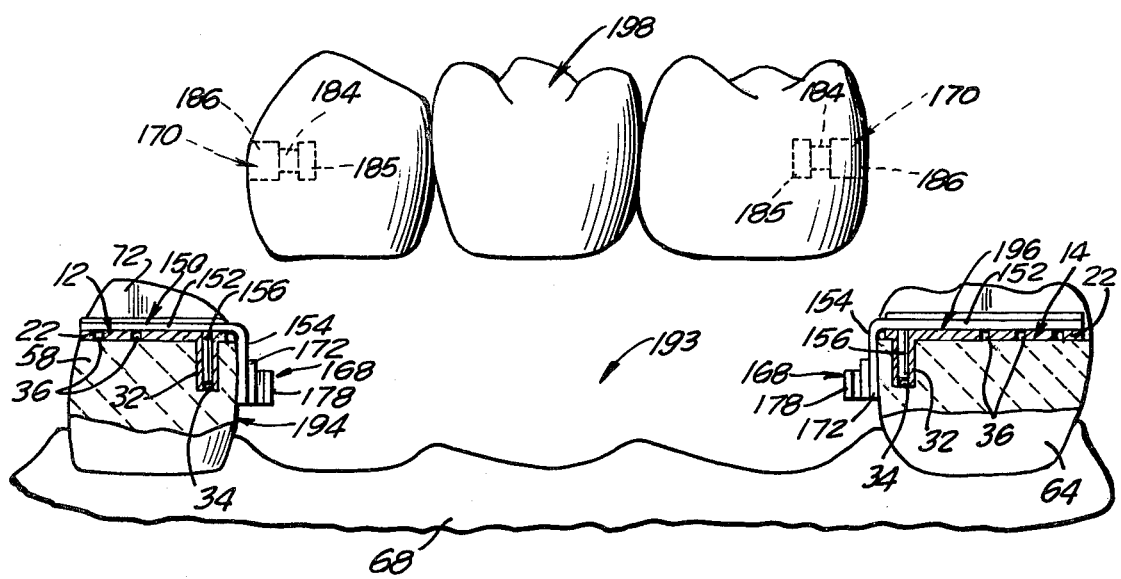
FIG. 13 is a fragmented elevational view, partly in section, of the embodiment shown in FIG. 12, showing a pair of connectors of the type of FIG. 8 secured in place with a dental prosthesis removably positioned between supporting teeth.

Referring now to FIGS. 12 and 13, the bar-like body members 12, 14 are inserted into the respective channels 72, 78 as was heretofore described in connection with FIG. 2. In this case, there is shown a substantially larger space 193 between the supporting teeth 58, 64.

After the bar-like body members 12, 14 have been inserted, the strap 150, of the type shown in FIG. 8, is suitably installed within the bar-like body member 12.

The depending pin 156 is received within the axial opening 34 of the tubular member 32, and the arm 154 is positioned against the outer side 194 of the supporting tooth 58. In this manner, the male member 168 projects into the space 193 to receive the prosthesis. An identical strap 196 would be secured within the bar-like body member 14. The strap 196 will not be described since it is identical to the strap 150.

As shown in FIG. 13, a removable dental prosthesis 198 is constructed so as to fit into the space 193 between the supporting teeth 58 and 64. At the lateral end portions of the removable dental prosthesis 198, female members 170 are enclosed therein in a conventional manner well known in the dental art. In this way, as the removable prosthesis 198 is inserted in place, as shown in FIG. 13, it is downwardly moved so that the female members 170 of the securement device will engage onto the protruding male member 168, and the dental prosthesis 198 will thereby be secured in place. When it is desired to remove the prosthesis 198, it can easily be lifted up and taken out for cleaning, replacement or the like.

In utilizing the securement device as described, the male members 168 on the straps 150, 196 must be vertically aligned and parallel with respect to each other. In order to achieve such alignment, a suitable jig can be utilized, as for example, the type described in the aforementioned U.S. Pat. No. 4,348,151. Similarly, the female members 170 secured within the dental prosthesis 198 must also be aligned with respect to the male members 168 to permit easy insertion and removal of the prosthesis.

Although the embodiment of FIGS. 12, 13 utilize two supporting teeth on either side of the space 193, it should be appreciated that only a single supporting tooth, or for that matter, many supporting teeth could be utilized on each side of the space 193. The length of the bar-like body members 12, 14 as well as the straps 150, 196 can be suitably cut in situ so as to fit the teeth. Furthermore, the bend formed at the distal end of the straps 150, 196 to define the depending arm 154, can either be preformed, or alternately, the dentist in situ can bend the distal end so as to suitably fit over the edge of the supporting tooth.

Figure 14:
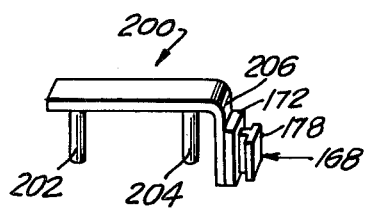
FIG. 14 is a perspective view showing a modification of the strap of FIG. 8, and showing two depending pins for additional retention.

Although a single tubular member 32 for each of the body members 12, 14 was described, it should again be understood that numerous tubular members can be utilized to provide additional retention. Specifically, as shown in FIG. 14, a modified strap 200 is shown to include two downwardly depending pins 202, 204 which are correspondingly received in the pair of tubular members 106, 108 depending from the bar-like body member 105, shown in FIG. 5. The bar-like body member 105 would in turn be utilized to form the two bores 110, 112, in accordance with the procedure heretofore described. The two bores 110, 112 are shown in a single tooth 114, and accordingly will provide additional support and retention, in a manner set forth above. Accordingly, the male member 168 is secured on the bent down arm 206 of the strap 200. The other cooperating strap is not shown, being identical to the strap 200.

Figure 16:
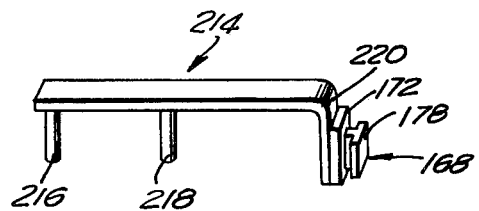
FIG. 16 is a perspective view of another modified strap of the type shown in FIG. 8 for use in splinting together adjacent teeth as well as for holding a removable dental prosthesis; and is a fragmented cross sectional elevational view showing the positioning of the modified strap of FIG. 16 in adjacent supporting teeth.
Figure 15:
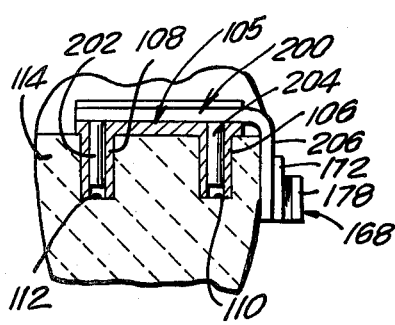
FIG. 15 is a fragmented cross sectional elevational view showing the positioning of the modified strap of FIG. 14 in a supporting tooth.
Figure 17:
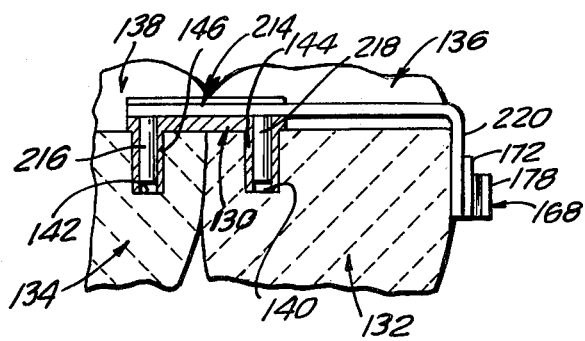

Alternately, as shown in FIGS. 16 and 18, another modified strap 214 is shown having two downwardly depending pins 216, 218, with the pin 218 being substantially spaced from the downwardly depending arm 220. In this embodiment, the pins 216, 218 would be respectively received within the tubular members 144, 146 which are secured in bores 140, 142 formed in respective adjacent teeth 132, 134, as shown in FIG. 7. In this embodiment, the bar-like body member 130 is utilized as a splint joining together the adjacent teeth 132, 134 in addition to providing the necessary support for the removable dental prosthesis, in a manner set forth above. Here again, the male member 168 is secured on the arm 220 of the strap 214. Again, the other cooperating strap is not shown, being identical to the strap 214.

It should be understood, that instead of the particular permanent or removable teeth shown herein, the dental prosthesis supported by the present invention could be a bridge or any other prosthesis requiring support from permanent teeth. It should also be appreciated that the particular dental prosthesis could be formed either by molding it in place, or by forming it with particular channels or openings for receiving portions of the connector of the present invention therein.

Although the method described for forming the bores in the teeth is in accordance with that utilizing the tubular members themselves, it should be understood that this method need not be utilized, and the bores could be formed in any other suitable manner so long as they accommodate the tubular members therein.

Numerous alterations of the structure herein disclosed will suggest themselves to those skilled in the art. However, it is to be understood that the present disclosure relates to preferred embodiments of the invention which are for purposes of illustration only and are not to be construed as a limitation of the invention.

What is claimed is:

1. A variable connector for supporting a dental prosthesis between opposing spaced apart supporting teeth, said connector comprising:
   a pair of elongated bar-like body members, each of said body members being disposable in its own respective channel in at least one supporting tooth on opposite sides of the prosthesis being supported;
   at least one tubular member depending from each body member for being received in a respective bore provided in the respective supporting tooth, each bore extending through a bottom wall of its respective channel, each tubular member including an axial opening extending therethrough;
   a pair of elongated straps each having at least one depending pin extending from a body portion of each strap, each of said straps being disposable over a respective body member with said pins extending into a respective axial opening of said tubular member of said respective body member, said straps terminating in arms which are disposed outwardly from their respective body portion and supporting tooth for supporting the dental prosthesis; and
   securing means on said arms located in the space between said supporting teeth for providing securement of said arms.

2. A variable connector as in claim 1, wherein said bar-like body members are trough shaped in cross section having side walls and a base wall, and wherein each of said straps is disposed between the side walls of a respective body member and substantially occupies the trough shape.

3. A variable connector as in claim 1, wherein two spaced apart tubular members extend from each body member, and correspondingly two pins depending from each strap for engagement in said two tubular members.

4. A variable connector as in claim 3, wherein said tubular members are spaced apart to be respectively received in a pair of spaced apart bores in each supporting tooth.

5. A variable connector as in claim 3, wherein two adjacent supporting teeth on at least one side of the prosthesis are retained, and wherein said two tubular members depending from a body member are spaced apart to be respectively received in a bore formed in each of the two adjacent supporting teeth, whereby said body member also defines a splint between the two adjacent teeth.

6. A variable connector as in claim 1, wherein said arms are respectively cantilevered from said body portions of said straps and extend into the space between the supporting teeth, the distal ends of said arms overlapping each other to define a continuous bridge across said space, and wherein said securing means includes a sleeve receiving said overlapping ends therein for securing together said overlapping ends of said arms.

7. A variable connector as in claim 6, wherein said arms are downwardly offset from said body portions of said straps so as to lie in a plane lower than said body portions of said straps.

8. A variable connector as in claim 6, wherein at least overlapping surfaces of said arms are serrated.

9. A variable connector as in claim 6, wherein said sleeve is crimped onto said overlapping ends of said arms.

10. A variable connector as in claim 1, wherein said arms are downwardly directed from said body portion of its respective strap to overlie a side of its supporting tooth, and wherein said securing means includes securement devices for removably securing the dental prosthesis between the supporting teeth, one section of each of said securement devices being disposed on each of said arms, the mating other section of each of said securement devices being retained by the dental prosthesis.

11. A variable connector as in claim 10, wherein each of said securement devices includes a male section secured onto a side of each downwardly directed arm, and a cooperating female section for securement within the dental prosthesis, said male section including a projecting member, said female section including a head portion having an inverted U-shaped housing for receiving said projecting member, internal side walls of said housing and external side walls of said projecting member being undercut to provide a tongue and groove engagement therebetween to removably support said prosthesis on said variable connector.

12. A variable connector as in claim 11, wherein each said male section includes a plate having one side thereof secured onto each of said downwardly directed arms, said projecting member extending from an opposite side of said plate.

13. A variable connector as in claim 11, wherein said female member includes a body portion coupled to said head portion, and an enlarged foot portion extending from an opposite end of said body portion, said body portion and foot portion assisting in securement of said female section within the dental prosthesis.

14. A variable connector as in claim 1, wherein a linear array of apertures is provided through each of said bar-like body members for selectively receiving fastening means for additional securement of each body member in its own channel.

* * * * *